(12) United States Patent
Smith et al.

(10) Patent No.: US 11,006,936 B2
(45) Date of Patent: *May 18, 2021

(54) CONTROL ASSEMBLIES FOR MEDICAL DEVICES AND RELATED METHODS OF USE

(71) Applicant: Boston Scientific Scimed, Inc., Maple Grove, MN (US)

(72) Inventors: Paul Smith, Smithfield, RI (US); Ray Hewenson Tong, Foxborough, MA (US); Jason Weiner, Grafton, MA (US); Naroun Suon, Lawrence, MA (US); Samuel Raybin, Marlborough, MA (US); David Graham, Reading, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 153 days.

This patent is subject to a terminal disclaimer.

(21) Appl. No.: 16/355,026

(22) Filed: Mar. 15, 2019

(65) Prior Publication Data

US 2019/0209149 A1 Jul. 11, 2019

Related U.S. Application Data

(63) Continuation of application No. 15/285,242, filed on Oct. 4, 2016, now Pat. No. 10,271,831.

(Continued)

(51) Int. Cl.
*A61B 17/00* (2006.01)
*A61B 1/018* (2006.01)
(Continued)

(52) U.S. Cl.
CPC .... *A61B 17/00234* (2013.01); *A61B 1/00133* (2013.01); *A61B 1/018* (2013.01);
(Continued)

(58) Field of Classification Search
CPC ........ A61B 17/00234; A61B 17/00133; A61B 17/34; A61B 17/3421; A61B 1/018
See application file for complete search history.

(56) References Cited

U.S. PATENT DOCUMENTS 10,271,831 B2 * 4/2019 Smith ................ A61B 17/3421
2005/0070754 A1 * 3/2005 Nobis .............. A61B 17/32056
600/16

(Continued)

FOREIGN PATENT DOCUMENTS

CN 104582600 A 4/2015
EP 2036505 A1 3/2009
(Continued)

*Primary Examiner* — Christopher J Beccia
(74) *Attorney, Agent, or Firm* — Bookoff McAndrews, PLLC

(57) ABSTRACT

A medical device may include a shaft, and a first tool extending from a distal end of the shaft. The medical device also may include a control assembly coupled to the shaft. The control assembly may include a console, a first grip extending proximally from the console, and a second grip extending proximally from the console. The control assembly also may include a first deflection actuator configured to deflect the first tool about a longitudinal axis of the first tool, a first rotation actuator configured to rotate the first tool about the longitudinal axis of the first tool, and a first longitudinal actuator configured to move the first tool along the longitudinal axis of the first tool.

19 Claims, 9 Drawing Sheets

Related U.S. Application Data

(60) Provisional application No. 62/237,860, filed on Oct. 6, 2015.

(51) Int. Cl.
*A61B 1/00* (2006.01)
*A61B 17/34* (2006.01)

(52) U.S. Cl.
CPC .. *A61B 17/3421* (2013.01); *A61B 2017/0034* (2013.01); *A61B 2017/00296* (2013.01); *A61B 2017/00309* (2013.01); *A61B 2017/00318* (2013.01); *A61B 2017/00323* (2013.01); *A61B 2017/00367* (2013.01); *A61B 2017/00371* (2013.01); *A61B 2017/00389* (2013.01); *A61B 2017/3449* (2013.01)

(56) References Cited

U.S. PATENT DOCUMENTS

| | | |
|---|---|---|
| 2014/0005478 A1 | 1/2014 | Kennedy et al. |
| 2014/0005708 A1* | 1/2014 | Shelton, IV ..... A61B 17/07207 606/170 |
| 2014/0107416 A1 | 4/2014 | Birnkrant |

FOREIGN PATENT DOCUMENTS

| | | |
|---|---|---|
| EP | 2559388 A1 | 2/2013 |
| JP | 2005-296412 A | 10/2005 |
| JP | 2014-523278 A | 9/2014 |

* cited by examiner

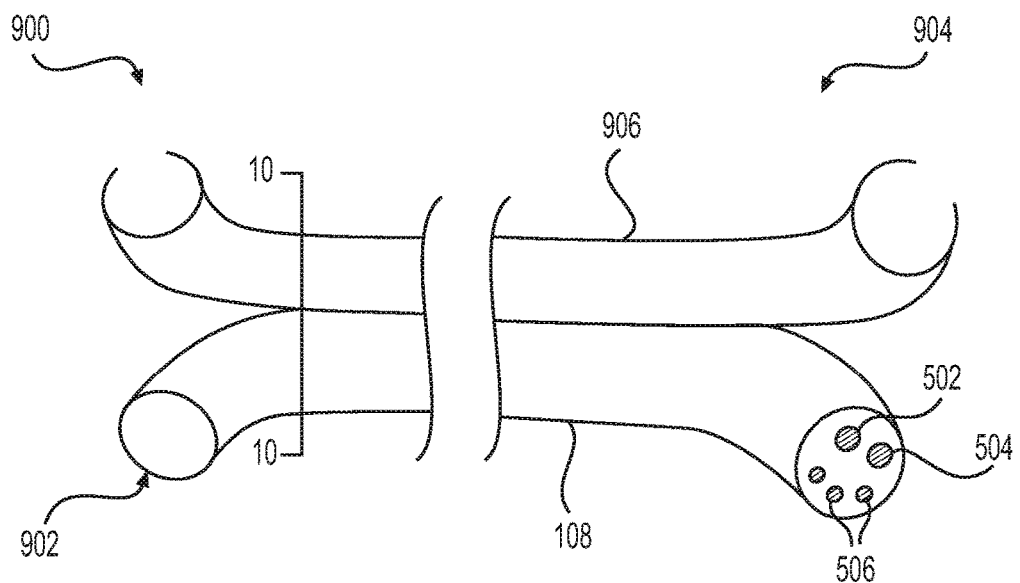
FIG. 9
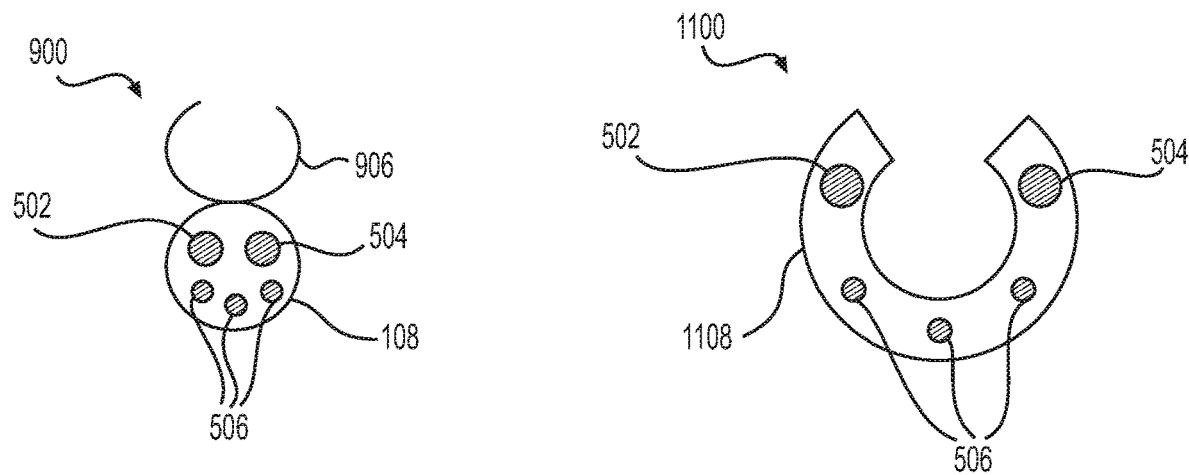
FIG. 10    FIG. 11

CONTROL ASSEMBLIES FOR MEDICAL DEVICES AND RELATED METHODS OF USE

CROSS-REFERENCE TO RELATED APPLICATION(S)

This patent application is a continuation of U.S. application Ser. No. 15/285,242, filed Oct. 4, 2016, now U.S. Pat. No. 10,271,831, which claims the benefit under 35 U.S.C. § 119 to U.S. Provisional Patent Application No. 62/237,860, filed on Oct. 6, 2015, the entireties of which are incorporated herein by reference.

TECHNICAL FIELD

Examples of the present disclosure relate to control assemblies for medical devices, and related methods of insertion and use.

BACKGROUND

Physicians are increasingly willing to perform more aggressive interventional and therapeutic endoscopic procedures including, but not limited to, removal of lesions (e.g., cancerous and other lesions), tunneling under the mucosal layer of the gastrointestinal tract to treat issues below the mucosa, full thickness removal of tissue (e.g., cancerous and other types), treatment of other organs by passing outside of the gastrointestinal tract (e.g., Natural Orifice Transluminal Endoscopic Surgery), endoscopic treatment and/or repair of post-surgical issues, such as post-surgical leaks, breakdown of surgical staple lines and/or anastomotic leaks, thoracic surgery, and airway or pleural space procedures, among others.

These complex procedures often require double-channel endoscopes to perform. However, many facilities do not have access to double-channel endoscopes. Articulating tools could also be applied to these procedures, but most designs are not ergonomically controllable with existing endoscopes. The extra degrees of freedom offered by articulating instruments are also difficult for a single physician to control.

SUMMARY

In one aspect the present disclosure is directed to a medical device that may include a shaft, and a first tool extending from a distal end of the shaft. The medical device also may include a control assembly coupled to the shaft. The control assembly may include a console, a first grip extending proximally from the console, and a second grip extending proximally from the console. The control assembly also may include a first deflection actuator configured to deflect the first tool about a longitudinal axis of the first tool, a first rotation actuator configured to rotate the first tool about the longitudinal axis of the first tool, and a first longitudinal actuator configured to move the first tool along the longitudinal axis of the first tool.

The first grip may be fixed relative to the console, and the second grip may be fixed relative to the first grip. The medical device may further include a first actuation assembly extending from the first deflection actuator to the first tool, wherein the first actuation assembly may include an actuating member extending through one or more lumens of the first actuation assembly. The actuation assembly may further include a first elongate member, and a second elongate member coupled to a distal end of the first elongate member, wherein the actuating member extends through respective lumens of the first elongate member and the second elongate member. The actuating member may be coupled to both the first deflection actuator and the first tool, and wherein movement of the first deflection actuator in a first direction may apply a distal force to the actuating member and causes the first tool to deflect from the longitudinal axis of the first tool along a first trajectory, and wherein movement of the first deflection actuator in a second direction opposite of the first direction may apply a proximal force to the actuating member and causes the first tool to deflect from the longitudinal axis of the first tool along a second trajectory that is opposite of the first trajectory. The first elongate member and the second elongate member may be rotatable relative to one another. The first rotation actuator may include a lumen, and the second elongate member may extend through the lumen. The lumen of the first rotation actuator and a portion of the outer surface of the second elongate member may be keyed to one another. Rotation of the rotation actuator may rotate the second elongate member, causing the first tool to rotate about the longitudinal axis of the first tool. The medical device may further include a first gear disposed within the console, wherein the first gear is movable by actuation of the first longitudinal actuator, and further including a rack coupled to an outer surface of the second elongate member, wherein the first gear engages the rack such that actuation of the longitudinal actuator causes the longitudinal movement of the first tool via the first gear and the rack. The second elongate member may further include a resilient portion disposed proximally of the rack and distally of the first rotation actuator. The medical device may further include a first cavity defined in one or more of the console or the first grip, and a first insert that is insertable into the first cavity, wherein the first deflection actuator is coupled to the first insert when the first insert is detached from the first cavity. At least one of the first grip and the second grip may be releasably coupled to the console. The first rotation actuator may extend from a proximal surface of the control assembly, the first deflection actuator extends from a top surface of the control assembly that is offset from the proximal surface, and the first longitudinal actuator may extend from a bottom surface of the control assembly offset from both the top surface and the bottom surface, wherein the proximal surface is disposed between the top surface and the bottom surface. The medical device may further include a second tool extending from the distal end of the shaft, a second deflection actuator configured to deflect the second tool about a longitudinal axis of the second tool, a second rotation actuator configured to rotate the second tool about the longitudinal axis of the second tool, and a second longitudinal actuator configured to move the second tool along the longitudinal axis of the second tool. The first grip may be configured to be held by a first hand of an operator and the second grip may be configured to be held by a second hand of the operator. The first deflection actuator, the first rotation actuator, and the first longitudinal actuator may be configured to be controlled by only fingers of the first hand while the second deflection actuator, the second rotation actuator, and the second longitudinal actuator may be configured to be controlled by only fingers of the second hand. The first rotation actuator and the second rotation actuator may each be disposed between the first grip and the second grip. The medical device may further include a split tube having a longitudinal opening extending along a substantial entirety of the split tube. The split tube may be configured to wrap around a shaft of an endoscope to secure the medical device to the endoscope.

In another aspect, the present disclosure is directed to a medical device that may include a shaft, a first tool extending from a distal end of the shaft, a second tool extending from the distal end of the shaft, and a control assembly coupled to the shaft. The control assembly may have a longitudinal axis and may include a first set of controls disposed on a first grip on a first side of the longitudinal axis of the control assembly. The first set of controls may be configured to control the deflection of the first tool from a longitudinal axis of the first tool, to control the rotation of the first tool about the longitudinal axis of the first tool, and to control movement of the first tool along the longitudinal axis of the first tool. The control assembly also may include a second set of controls disposed on a second grip on a second side of the longitudinal axis of the control assembly that is opposite of the first side. The second set of controls may be configured to control the deflection of the second tool from a longitudinal axis of the second tool, to control the rotation of the second tool about the longitudinal axis of the second tool, and to control movement of the second tool along the longitudinal axis of the second tool.

The first set of controls and the second set of controls may be mirror images of one another about the longitudinal axis of the control assembly.

In yet another aspect, the present disclosure is directed to a method of performing a surgical procedure. The method may include inserting a shaft into a patient. The shaft may be coupled to a control assembly at a proximal end. The control assembly may have a console, a first grip extending from the console, and a second grip extending from the console. A first tool and a second tool may extend distally from the shaft, the control assembly may further include a first set of controls for controlling the first tool and a second set of controls for controlling the second tool. The method may include gripping the first grip with a first hand, and actuating the first set of controls with only fingers from the first hand. The method also may include gripping the second grip with a second hand, and actuating the second set of controls with only fingers from the second hand.

The first grip may be fixed relative to the console, and the second grip may be fixed relative to the first grip. Actuating the first set of controls with only fingers from the first hand may occur simultaneously with actuating the second set of controls with only fingers from the second hand.

BRIEF DESCRIPTION OF THE DRAWINGS

The accompanying drawings, which are incorporated in and constitute a part of this specification, illustrate various examples and together with the description, serve to explain the principles of the disclosed examples.

FIG. 9 is a side view of a medical device according to another example of the present disclosure.

FIG. 10 is a cross-sectional view of the medical device of FIG. 9 taken along line 10-10.

FIG. 11 is an end view of a medical device according to yet another example of the present disclosure.

DETAILED DESCRIPTION

Reference will now be made in detail to examples of the present disclosure, examples of which are illustrated in the accompanying drawings. Wherever possible, the same reference numbers will be used throughout the drawings to refer to the same or like parts or components. The term "distal" refers to the direction that is away from the user or operator and into the patient's body. By contrast, the term "proximal" refers to the direction that is closer to the user or operator and away from the patient's body.

Figure 1:
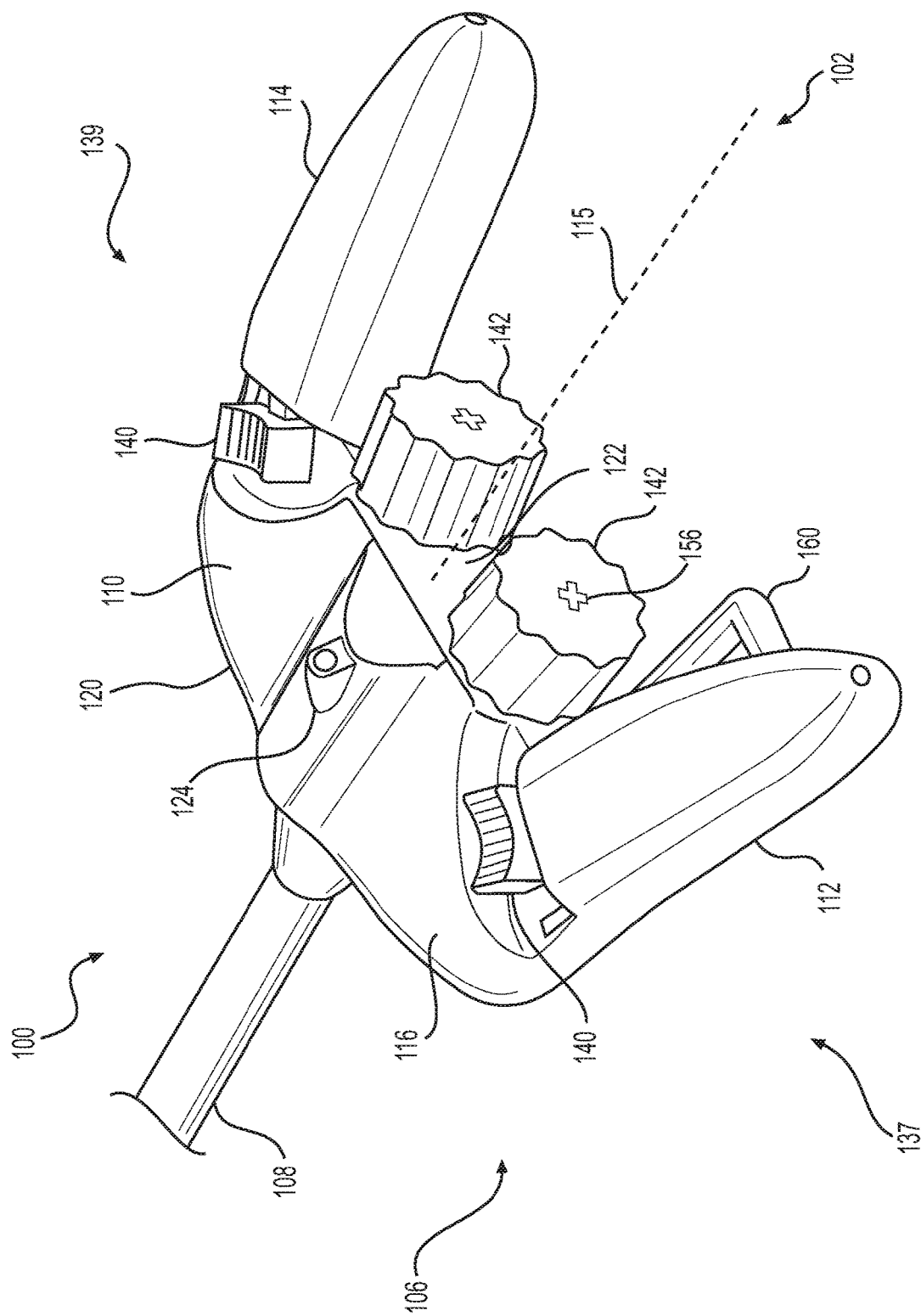
FIG. 1 is a perspective view of a control assembly according to an example of the present disclosure.
Figure 2:
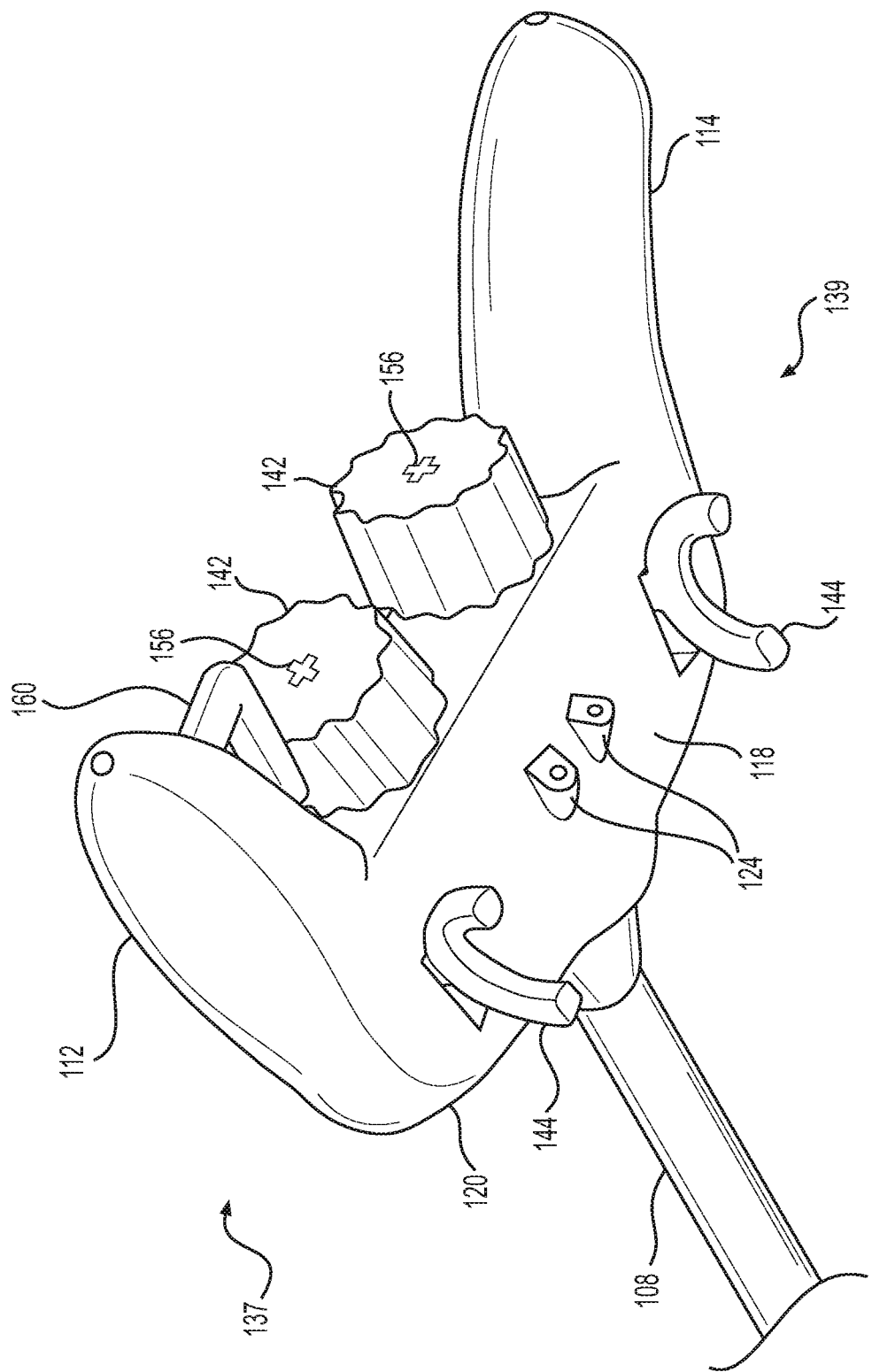
FIG. 2 is another perspective view of the control assembly of FIG. 1.
Figure 3:
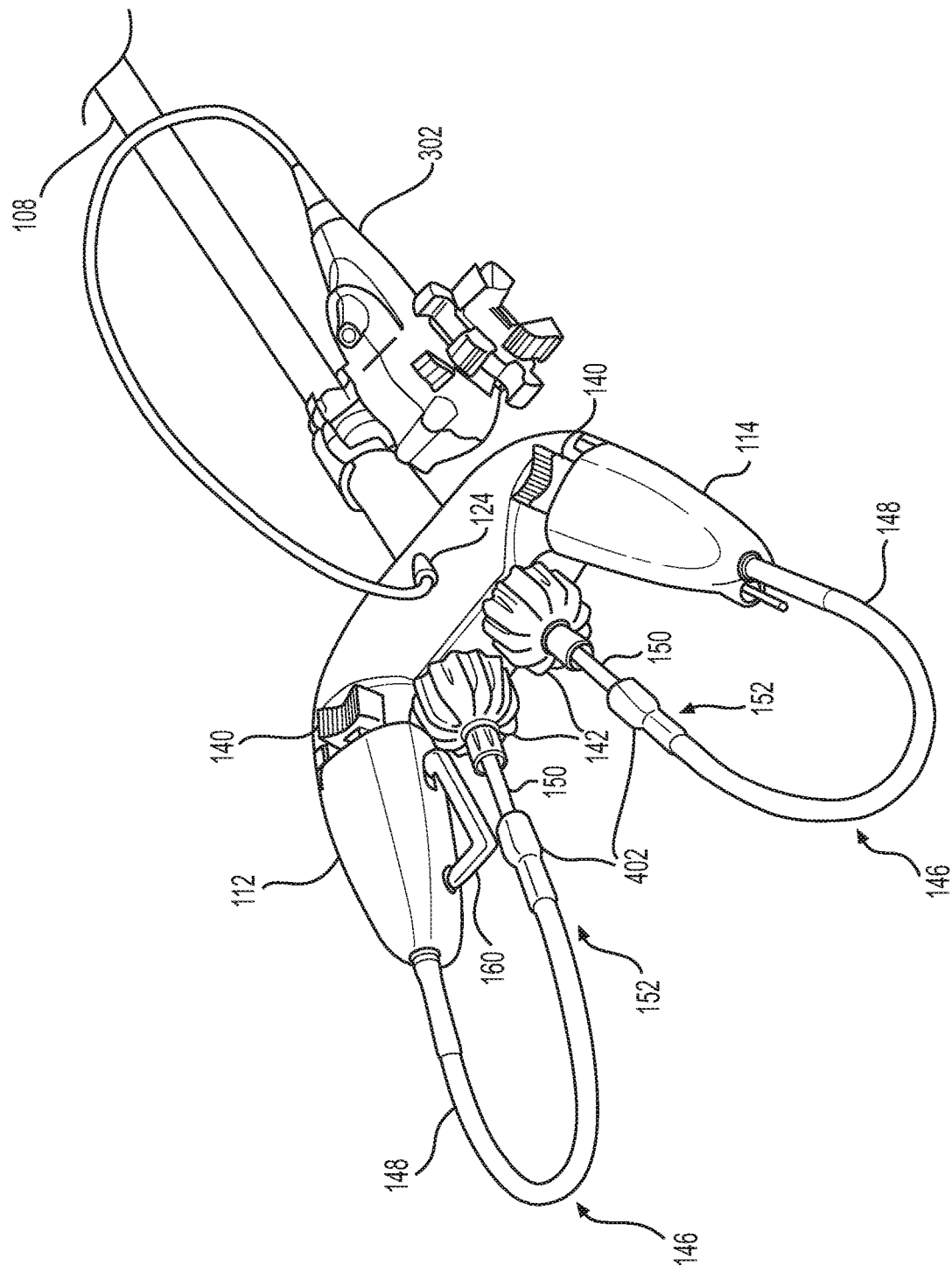
FIG. 3 is yet another perspective view of the control assembly of FIG. 1.

A medical device 100 is shown in FIGS. 1-5. Medical device 100 may be an endoscopic device configured to allow an operator to access and view internal body anatomy of a patient as well as to insert medical tools into the body to perform medical procedures. Medical device 100 may extend from a proximal end 102 toward a distal end 104 (shown only in FIG. 5). Referring to FIGS. 1 and 2, a control assembly 106 may be disposed at proximal end 102 of medical device 100. A shaft 108 may extend distally from the control assembly 106.

Figure 5:
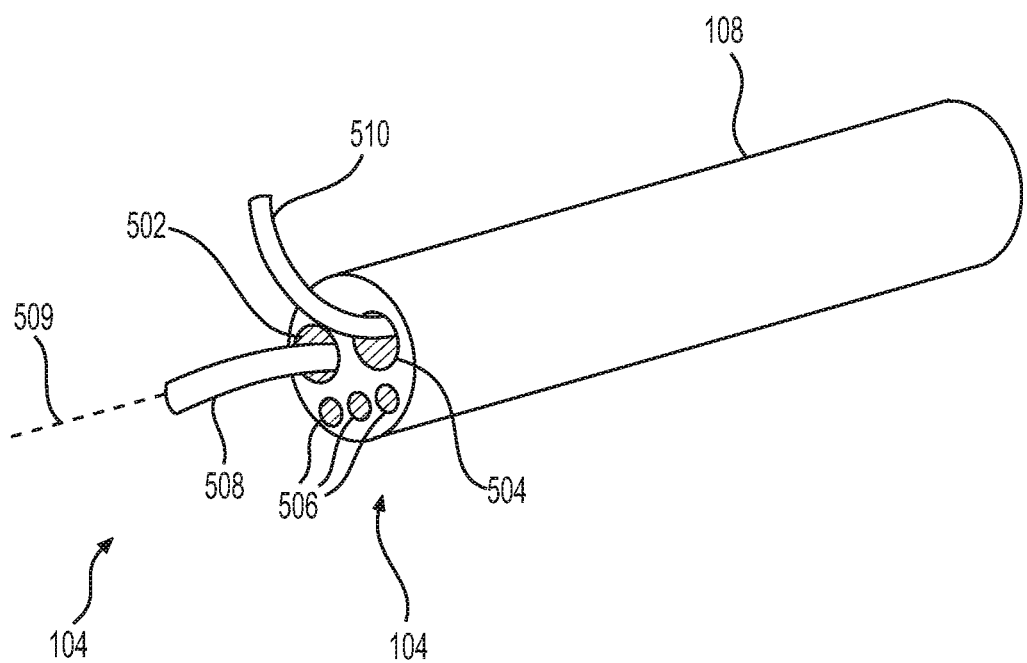
FIG. 5 is a perspective view of a distal end of a medical device according to an example of the present disclosure.

Control assembly 106 may be configured to be grasped by a single operator with two hands to control one or more articulating instruments disposed at distal end 104 of medical device 100 (e.g., a first tool 508 and a second tool 510 shown in FIG. 5). Control assembly 106 may include a console 110 and grips 112 and 114 that extend proximally from console 110. Grips 112 and 114 also may extend radially away from a longitudinal axis 115 of control assembly 106 in opposite directions (i.e., the longitudinal axes of grips 112, 114 may be transverse to longitudinal axis 115), and may generally be mirror-images of one another about longitudinal axis 115. Console 110 and grips 112 and 114 may be contiguously formed with one another as a single piece of material or combination of materials. In another example, console 110 and grips 112 and 114 may be formed as a clamshell or other suitable container having multiple exterior pieces coupled to one another. Once assembled, grip 112 may be fixed relative to console 110 (including during actuation), and grip 114 may be fixed relative to grip 114. As such, grip 114 also may be fixed relative to console 110. Console 110 may include a top surface 116, a bottom surface 118 (shown only in FIG. 2), a distal surface 120, and a proximal surface 122. Each of surfaces 116, 118, 120, and 122 may be offset from one another. Top surface 116 may be coupled to bottom surface 118 at a proximal end by proximal surface 122, and at a distal end by distal surface 120. Console 110 may be formed of any suitable material or combination of materials, such as, e.g., one or more polymers, metals, alloys, and the like. In some examples, the surfaces of one or more of console 110 and grips 112 and 114 may be roughened, notched, slotted, etched, sand-blasted, coated or otherwise modified to provide a better gripping surface.

Referring to FIG. 5, shaft 108 may be flexible in order to navigate tortuous anatomy within a patient. In some examples, shaft 108 may be uniformly flexible, or may include portions having varied flexibility. For example, a distal end of shaft 108 may be more flexible than a proximal end of shaft 108. Shaft 108 may include any suitable dimensions as is known in the art, and may be used in place of or in combination with any traditional medical scope, such as, e.g., an endoscope, a ureteroscope, a colonoscope, a hysteroscope, a uteroscope, a bronchoscope, or a cystoscope. Shaft 108 may be directly inserted into the body of a patient or may be extended over a guidewire using one or more lumens. Shaft 108 also may be inserted into a laparoscopic port, a single incision port, an over-tube, a bouche, or any other suitable member.

Referring to FIG. 5, shaft 108 may include multiple lumens extending therethrough, for example, a lumen 502, a lumen 504, and additional lumens 506. Although the depicted embodiment of medical device 100 has five lumens, any other suitable number of lumens is also contemplated. Lumens 502, 504, and 506 may have any suitable length, size, cross-sectional area, shape, and/or configuration, and may extend along at least a portion of the length of shaft 108. In one example, one or more of the lumens may extend substantially along the entire length of shaft 108.

As shown in FIG. 5, each of lumens 502 and 504 may be configured to accommodate one tool extending therethrough. For example, first tool 508 may extend through lumen 502, while a second tool 510 may extend through lumen 504 (shown in FIG. 5).

At least one lumen 506 may be configured to accommodate any suitable visual device. For example, a lumen 506 may be configured to contain a visual device allowing a user to view an area adjacent to distal end 104 of medical device 100, including areas distal to distal end 104. The visual device may be built into medical device 100, and include one or more of a light source, lens, fiber optics, and/or any suitable electronic vision components known in the art, etc., to view a work site within a patient's body lumen. In another example, a separate imaging device 302 (shown in FIG. 3) may be utilized. Imaging device 302 may be a pediatric endoscope equipped with an imaging device. It is also contemplated that lumens 506 may be utilized for any other suitable purpose, such as, e.g., irrigation, aspiration, suction, delivery of additional tools, delivery of therapeutics, or as a guiding lumen which is used to guide shaft 108 over a guidewire.

Lumens 506 may be accessed by one or more ports 124 disposed on control assembly 106. In one example, a port 124 may be disposed on top surface 116 of control assembly 106, and two ports 124 may be disposed on bottom surface 118 of control assembly 106. It is contemplated that ports 124 may be disposed in any suitable location along control assembly 106. The various ports 124 may include one or more differentiating markings (not shown) to help an operator identify the function of a given port 124, and/or to associate a given port 124 with a given lumen 506. For example, corresponding ports 124 and lumens 506 may have corresponding or identical markings. The markings also may include descriptive text which may indicate to an operator the purpose or functionality of a given port or actuator.

Tool Manipulation

As noted above, medical device 100 may be configured to allow an operator to manipulate both first tool 508 and second tool 510 using control assembly 106. The articulation of first tool 508 may be controlled by a first control set 137 that includes a deflection actuator 140, a rotational actuator 142, a longitudinal actuator 144, a gear 145, and an actuating assembly 146. Actuating assembly 146 may include a first elongate member 148 coupled to a second elongate member 150 at a rotary joint 152, and an actuating member 154 that extends through respective lumens of first elongate member 148 and second elongate member 150. A second control set 139 may include one or more of the same components of first control set 137, and may be configured to control the articulation of second tool 510.

Actuating member 154 may be translatable within first elongate member 148 and second elongate member 150. Thus, in at least some examples, first elongate member 148, second elongate member 150, and actuating member 154 may form a Bowden-type cable. Actuating member 154 may be coupled at a first end to deflection actuator 140 within grip 112, and may extend through actuating assembly 146, where actuating member 154 may be coupled at a second end to first tool 508. Actuating member 154 may be any suitable actuating member such as, e.g., a wire, cable, or the like.

Figure 4:
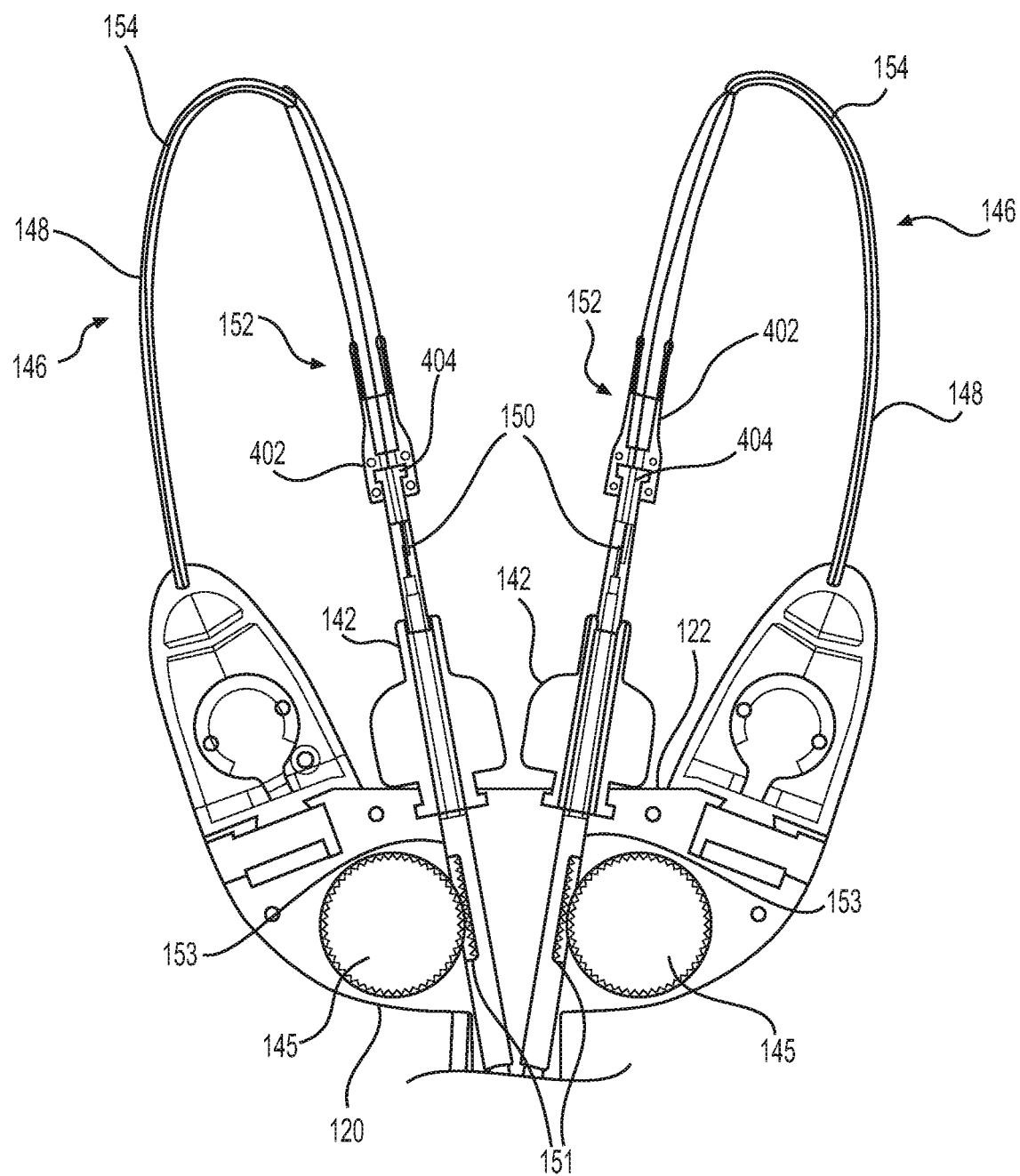
FIG. 4 is a cutaway view of the control assembly of FIG. 1.

First elongate member 148 may be coupled and/or fixed to a proximal end of grip 112, and a lumen of first elongate member 148 may communicate with a lumen (not shown) disposed through grip 112. Actuating member 154 may extend through these lumens. A distal end of first elongate member 148 may be coupled to second elongate member 150 at rotary joint 152. Rotary joint 152 may be formed by corresponding features from the distal end of first elongate member 148 and a proximal end of second elongate member 150. As shown in FIG. 4, first elongate member 148 may include a housing 402 configured to receive a coupling 404 disposed at the proximal end of second elongate member 150. Housing 402 and coupling 404 may be shaped to allow for the rotation of coupling 404 within a cavity of housing 402. Coupling 404 may have any suitable shape such as, e.g., spherical, cylindrical, conical, or the like, and housing 402 may include a correspondingly-shaped cavity. It is further contemplated that housing 402 may be disposed on second elongate member 150, while coupling 404 is disposed on first elongate member 148. Still further, rotary joint 152 may utilize any alternative structures to achieve relative rotation between first elongate member 148 and second elongate member 150.

Second elongate member 150 may extend distally from rotary joint 152, through a lumen 156 disposed through rotational actuator 142 (described below), through lumen 502, and may be coupled to first tool 508. First elongate member 148 and second elongate member 150 may be rotatable relative to one another about rotary joint 152. Second elongate member 150 may include features that are configured to interlock with a corresponding feature disposed on rotational actuator 142, as further described below. In some examples, at least a portion of second elongate member 150 may have a cross-sectional profile configured to interact with a corresponding cross-sectional profile of rotational actuator 142. In one example, the portion of second elongate member 150 may include a t-shaped cross-sectional profile, a star-shaped cross-sectional profile, a rectangular cross-sectional profile, an irregular cross-sectional profile, or any other suitable cross-sectional profile. In some examples, the portion of second elongate member 150 may have a non-circular cross-sectional profile. Second elongate member 150 also may include a gear 151 (e.g., a rack gear) disposed on an outer surface of elongate member 150.

Additionally, at least a portion of second elongate member 150 may be resilient and flexible along a longitudinal axis of second elongate member 150. In one example, a resilient portion 153 may be disposed proximally of gear 151 and distally of rotation actuator 142. In one example, resilient portion 153 may be a spring integrated into second elongate member 150. That is, the spring may be defined at a proximal end and at a distal end by non-resilient, or less-resilient portions of second elongate member 150. The spring may include stainless steel or another metal, or may include a polymeric material such as, e.g., polyethylene (PE), polypropylene (PP), polyvinylchloride (PVC) or polytetrafluoroethylene (PTFE). In another example, the resilient portion 153 may not be a spring, but may be a portion of second elongate member formed from a resilient material including polymeric and/or synthetic foams, rubber, and silicone and/or elastomers.

Deflection actuator 140 may be configured to control the deflection of first tool 508 about longitudinal axis 509 of first tool 508. Deflection actuator 140 may be any suitable actuator that is configured to apply forces in opposite directions to actuating member 154 in order to articulate first tool 508 in opposing trajectories. For example, deflection actuator 140 may be configured such that when a force is applied to deflection actuator 140 in a first direction, first tool 508 may deflect along a first trajectory away from the longitudinal axis 509. When a force is applied to deflection actuator 140 in a second direction that is opposite of the first direction, first tool 508 may deflect along a second trajectory from the longitudinal axis 509 that is opposite of the first trajectory. In some examples, when a force is applied to deflection actuator 140 in the first direction, deflection actuator 140 may apply a proximal pulling force on actuating member 154. However, when a force is applied to deflection actuator 140 in the second direction, deflection actuator 140 may apply a distal pushing force on actuating member 154. Deflection actuator 140 may utilize any suitable mechanism to apply force to actuating member 154. In some examples, deflection actuator 140 may be a sliding element or a pivoting element.

Rotational actuator 142 may be configured to control the rotation of first tool 508 about the longitudinal axis 509. Rotational actuator 142 may be a knob or other suitable rotational actuator, and may be coupled to or otherwise extend from proximal surface 122 of console 110, or rotational actuator 142 may be disposed in any other suitable location. Rotational actuator 142 may include a lumen 156 having a cross-section that is keyed to or that otherwise corresponds to the cross-section of at least a portion of second elongate member 150 as set forth above. When an operator rotates rotational actuator 142, the shape of lumen 156 may interact with the shape of a portion of second elongate member 150, causing second elongate member 150 to rotate with rotational actuator 142, and also causing first tool 508 to rotate about the longitudinal axis of first tool 508. For example, an edge defining lumen 156 may abut or otherwise engage an edge of the outer surface of second elongate member 150. When rotational actuator 142 is rotated in a first rotational direction (e.g., clockwise), first tool 508 may rotate along the first rotational direction (e.g., clockwise). However, when rotational actuator 142 is rotated in a second rotational direction (e.g., counter-clockwise), first tool 508 may rotate in the second rotational direction (e.g., counter-clockwise). Rotational actuator 142 may be coupled to second elongate member 150 by other mechanisms such that rotation of rotational actuator 142 causes a corresponding rotation of second elongate member 150. For example, clamps, hinges, adhesives, or other suitable fastening mechanisms may be utilized to couple rotational actuator 142 to second elongate member 150.

Longitudinal actuator 144 may be disposed on bottom surface 118 of control assembly 106, and may be configured to control the translation of first tool 508 along the longitudinal axis 509. Longitudinal actuator 144 may be directly coupled to second elongate member 150, causing second elongate member 150 to move in a longitudinal direction when longitudinal actuator 144 is moved in a longitudinal direction. The longitudinal movement of second elongate member 150 then may cause a longitudinal movement of first tool 508. For example, longitudinal actuator 144 may be configured to move gear 145 in a first direction, and in a second direction that is opposite the first direction. Gear 145 may drive gear 151 disposed on the outer surface of second elongate member 150. When the longitudinal actuator 144 is moved in the first direction, second elongate member 150 (and first tool 508) may move along a first longitudinal path (e.g., distally), and when the longitudinal actuator 144 is moved in the second direction, second elongate member 150 (and first tool 508) may move along a second longitudinal path (e.g., proximally).

Control assembly 106 may include additional actuators, such as, e.g., a trigger 160 that is disposed along a lateral surface of grip 112. Trigger 160 may be configured to actuate jaws (or other end effectors) of first tool 508 when first tool 508 is, for example, a cutting member, forceps, grasper, or other suitable member having multiple parts that are articulatable relative to one another. Trigger 160 may extend outward from a lateral surface of grip 112. In the embodiment shown, trigger 160 is shown extending from grip 112 toward longitudinal axis 115 and grip 114. However, trigger 160 could extend in other directions, such as away from longitudinal axis 115. Trigger 160 may move radially inward and outward from grip 112 in response to a force applied by an operator. For example, to actuate first tool 508, an operator may clench trigger 160 with one or more fingers, and may release trigger 160 to deactivate or otherwise return first tool 508 to its original state. In one example, trigger 160 may be attached to actuating member 154, and elongate member 148 may be anchored relative to trigger 160. A portion of trigger 160 attached to actuating member 154 may trace a short arc which is approximately linear and axially aligned to actuating member 154, thereby moving actuating member 154 relative to elongate member 148 when trigger 160 is actuated. This actuation may move an end effector coupled to the distal end of actuating member 154. In an alternative example, a spring-loaded linear actuating element may be used instead of a pivoting trigger.

As noted above, control assembly 106 may include both a first control set 137 and a second control set 139 configured to actuate first tool 508 and second tool 510, respectively. In one example, the first control set 137 may be actuated with one hand (e.g., the left hand of the operator), while the second control set may be actuated with the other hand (e.g., the right hand of the operator). First control set 137 may be disposed on a first side of longitudinal axis 115, and second control set 139 may be disposed on a second, opposing side of longitudinal axis 115. One or more components from the first and second control sets 137 and 139 may be symmetrical to one another about the longitudinal axis 115. For example, the deflection actuator 140 of first control set 137 may be symmetric about longitudinal axis 115 to the deflection actuator 140 of second control set 139. Further, the rotational actuator 142 of the first control set 137 may be symmetric about longitudinal axis 115 to the rotational actuator 142 of the second control set 139. Still further, the longitudinal actuator 144 of the first control set 137 may be symmetric about longitudinal axis 115 to the longitudinal actuator 144 of second control set 139. In some examples, however, these components may not be symmetric to one another.

In some examples, first control set 137 may be operated with only the fingers (including the thumb) of a first hand of an operator, while the second control set 139 may be operated simultaneously with only the fingers (including the thumb) of a second hand of an operator. Deflection actuator 140 of first control set 137 may be operated by the left thumb, and deflection actuator 140 of second control set 139 may be operated by the right thumb. Rotation actuator 142 of first control set 137 may be operated by the left thumb and left index finger. Rotation actuator 142 of second control set 139 may be operated by the right thumb and right index finger. Alternatively, the operator may rotate the rotation actuators by another suitable combination of fingers. Longitudinal actuators 144 may be operated by the index finger of a given hand of an operator (left or right). For example, the longitudinal actuator 144 of first control set 137 may be operated with the left index finger while the longitudinal actuator 144 of second control set 139 may be operated with the right index finger.

Figure 6:
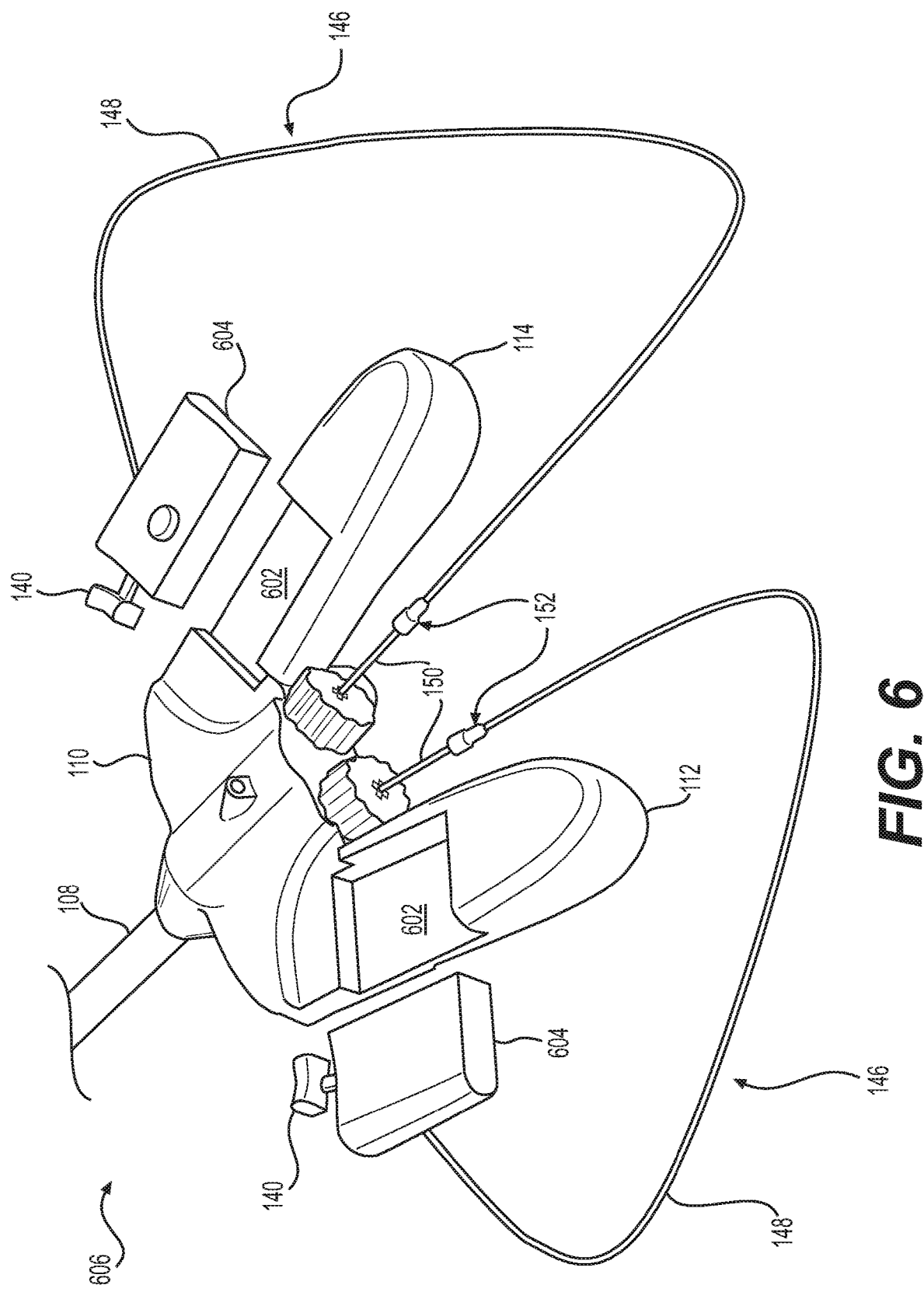
FIG. 6 is a partially exploded view of a control assembly according to another example of the present disclosure.

A control assembly 606 is shown in FIG. 6 which is substantially similar to control assembly 106 described above, except that control assembly 606 may include one or more cavities 602 that are configured to receive a corresponding insert 604. The cavities 602 may be disposed in either grip 112 and grip 114, in console 110, or in one or more of grip 112 and grip 114 and console 110. Insert 604 may include deflection actuator 140 that is configured to deflect first tool 508 (or second tool 510) from the longitudinal axis of those respective tools. In the embodiment of FIG. 6, actuating assembly 146 may extend from a lateral surface of insert 604, or otherwise may extend from a surface of insert 604 that is exposed when insert 604 is disposed within cavity 602. Insert 604 and cavity 602 may be coupled together by any suitable mechanism including, e.g., snap fits and other engagements. The example shown in FIG. 6 may also utilize a trigger 160 substantially similar to the one described with reference to FIGS. 1 and 2 above in order to activate a tool or end effector.

Figure 7:
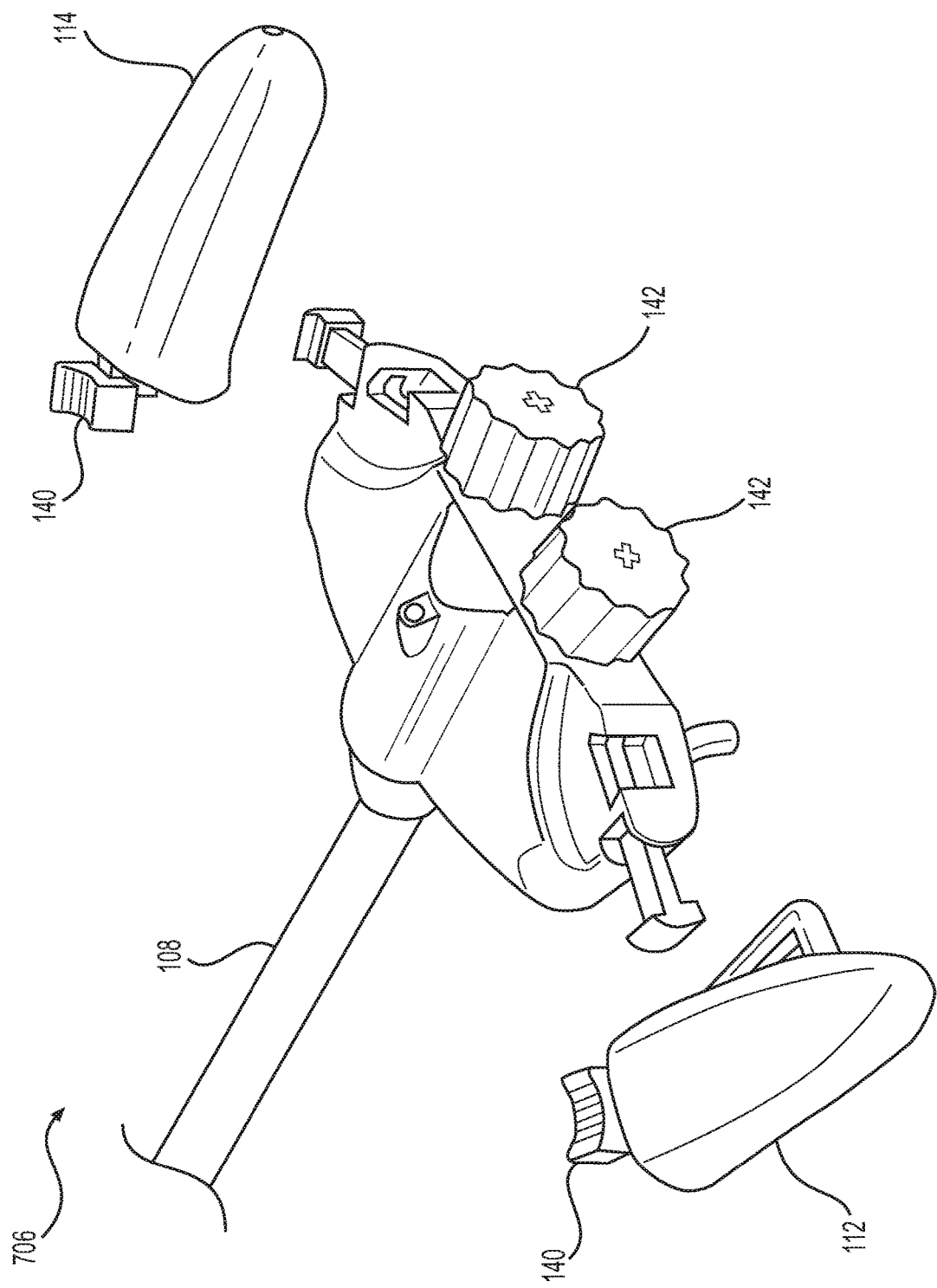
FIG. 7 is a partially exploded view of a control assembly according to yet another example of the present disclosure.

A control assembly 706 is shown in FIG. 7 which is substantially similar to control assembly 106 described above, except that grips 112 and 114 of control assembly 706 may be detachable from console 110. Grips 112 and 114 may be coupled to console 110 by a snap fit or other suitable engagement. In the embodiment shown in FIG. 7, deflection actuators 140 may be directly coupled to the detachable grips 112 and 114.

Figure 8:
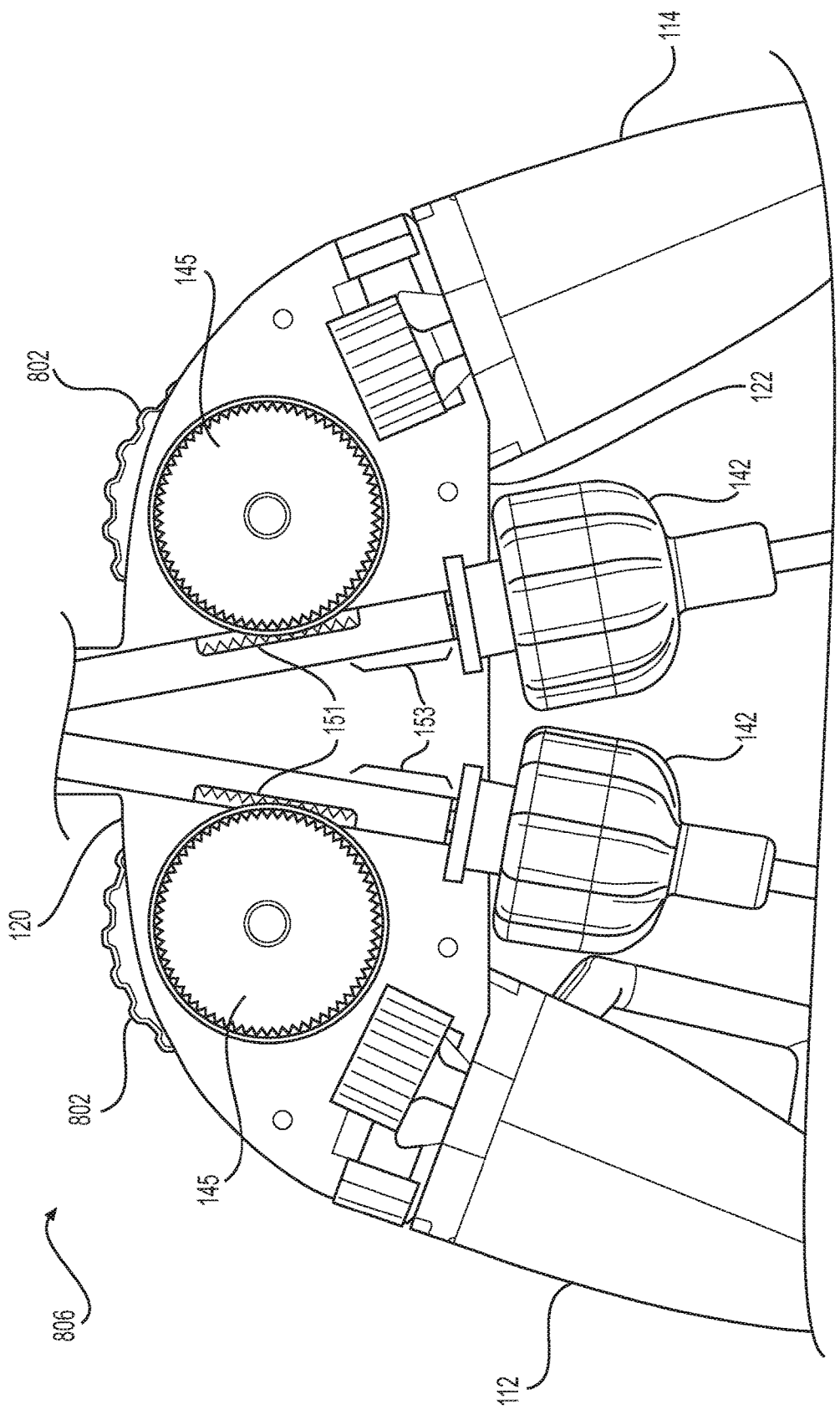
FIG. 8 is a partially cutaway view of a control assembly according to yet another example of the present disclosure.

A control assembly 806 is shown in FIG. 8, which is substantially similar to control assembly 106 described above, except that longitudinal actuators 144 are replaced by wheels 802 that extend from distal surface 120 of control assembly 106. The rotation of wheels 802 may rotate gears 145 to drive the longitudinal movement of second elongate member 150, and tools 508, 510 via gears 151.

A medical device 900 is shown in FIGS. 9 and 10, which may extend from a proximal end 902 to a distal end 904. Medical device 900 may include a shaft 108, and a split tube 906. Split tube 906 may be an elongate member extending from proximal end 902 to distal end 904 that is configured to wrap around a shaft of an endoscopic member, such as, e.g., an endoscope, bronchoscope, or the like. Split tube 906 may include a longitudinal opening 910 that extends along a substantial entirety of the length of split tube 906. The opening 910 may allow split tube 906 to be placed around the shaft of an endoscopic member. Split tube 906 may be fixed to shaft 108 along a substantial entirety of the length of medical device 900. In some examples, split tube 906 and shaft 108 may not be coupled to one another at proximal end 902 and distal end 904 such that split tube 906 and shaft 108 are movable relative to one another at those uncoupled regions. Once disposed around the shaft of an endoscope, split tube 906 may be secured to the endoscope shaft in any suitable manner, such as, e.g., friction fits, clamps, or the like.

A medical device 1100 is shown in FIG. 11. Medical device 1100 may include a shaft 1108 that is substantially similar to shaft 108 described above, except that shaft 1108 may itself be a split tube having an opening 1110 that extends along a substantial entirety of the length of shaft 1108. Thus, shaft 1108 may be configured to wrap around the shaft of an endoscope in a similar manner as split tube 906. The proximal end (not shown) of elongate member 1108 may be coupled to a control assembly 106 (described above) in order to allow an operator to control the articulation of tools disposed at the distal end of the medical device 1100.

Medical devices 900 and 1100 may include one or more of the functionalities of medical device 100 set forth above, and may additionally be used in conjunction with a traditional endoscopic device, effectively using the traditional endoscope shaft as a guidewire. This configuration also may allow for the omission of certain functionalities from medical devices 900 and 1100, such as, e.g., imaging, if such functionalities are present on the paired endoscopic device. This may reduce the manufacturing costs of medical devices 900 and 1100, allowing practitioners to utilize medical devices 900 and 1100 in conjunction with existing equipment.

The medical device disclosed herein may allow the operator to control all degrees of freedom of two articulating instruments (e.g., first and second tools 508 and 510) using only their fingers. Control of first and second tools 508 and 510 may not require any large muscle groups such as arms, wrists, or elbow movement. The disclosed medical devices also may not require any additional support except for the support of the operator's hands. The operator holding the control assembly 106 may be able to resist all digit input forces applied to the user interface with the hands applying the load. That is, the operator's hands may act as an anchor relative to which a significant portion of the actuation occurs, instead of the device requiring an anchor to a stand or other rigid structure.

The disclosed medical device may allow some degrees of freedom to be kept on the reusable or semi-reusable console 110. The reusability of various components may reduce the long-term costs of using the disclosed medical devices.

Those skilled in the art will understand that the medical devices set out above can be implemented in any suitable body lumen (e.g., blood vessels, the biliary tract, urological tract, gastrointestinal lumens, and the like) without departing from the scope of the disclosure as defined by the claims. In particular, constructional details, including manufacturing techniques and materials, are well within the understanding of those of skill in the art and have not been set out in any detail here. These and other modifications and variations are well within the scope of the present disclosure and can be envisioned and implemented by those of skill in the art.

Other examples of the present disclosure will be apparent to those skilled in the art from consideration of the specification and practice of the examples disclosed herein. It is intended that the specification and examples be considered as exemplary only, and departures in form and detail may be made without departing from the scope and spirit of the present disclosure as defined by the following claims.

What is claimed is:

1. A medical device, comprising:
    a shaft;
    a first tool extending from a distal end of the shaft; and
    a control assembly coupled to the shaft, the control assembly including:
        a console,
        a first grip extending proximally from the console;
        a second grip extending proximally from the console:
        a first deflection actuator configured to deflect the first tool about a longitudinal axis of the first tool; and
        a first actuation assembly extending from the first deflection actuator to the first tool, wherein:
            the first actuation assembly includes an actuating member extending through one or more lumens of the first actuation assembly;
            the first actuation assembly further includes a first member, and a second member coupled to a distal end of the first member; and
            the actuating member extends through respective lumens of the first member and the second member.

2. The medical device of claim 1, wherein the first grip is fixed relative to the console, and the second grip is fixed relative to the first grip.

3. The medical device of claim 1, wherein the actuating member is coupled to both the first deflection actuator and the first tool, and wherein movement of the first deflection actuator in a first direction applies a distal force to the actuating member and causes the first tool to deflect from the longitudinal axis of the first tool along a first trajectory, and wherein movement of the first deflection actuator in a second direction opposite of the first direction applies a proximal force to the actuating member and causes the first tool to deflect from the longitudinal axis of the first tool along a second trajectory that is opposite of the first trajectory.

4. The medical device of claim 1, wherein the first member and the second member are rotatable relative to one another.

5. The medical device of claim 1, further including a first rotation actuator configured to rotate the first tool about the longitudinal axis of the first tool, wherein the first rotation actuator includes a lumen, and wherein the second member extends through the lumen of the first rotation actuator, wherein the lumen of the first rotation actuator and a portion of an outer surface of the second member are keyed to one another, and wherein rotation of the rotation actuator rotates the second member, causing the first tool to rotate about the longitudinal axis of the first tool.

6. The medical device of claim 1, further including a first longitudinal actuator configured to move the first tool along the longitudinal axis of the first tool and a first gear disposed within the console, wherein the first gear is movable by actuation of the first longitudinal actuator, and further including a rack coupled to an outer surface of the second member, wherein the first gear engages the rack such that actuation of the first longitudinal actuator causes the longitudinal movement of the first tool via the first gear and the rack.

7. The medical device of claim 6, wherein the second member further includes a resilient portion disposed proximally of the rack.

8. The medical device of claim 1, further including a first cavity defined in one or more of the console or the first grip, and a first insert that is insertable into the first cavity, wherein the first deflection actuator is coupled to the first insert when the first insert is detached from the first cavity.

9. The medical device of claim 1, wherein at least one of the first grip and the second grip is releasably coupled to the console.

10. The medical device of claim 1, further including:
    a second tool extending from the distal end of the shaft; and
    a second deflection actuator configured to deflect the second tool about a longitudinal axis of the second tool;
    wherein the first grip is configured to be held by a first hand of an operator and the second grip is configured to be held by a second hand of the operator, wherein first deflection actuator, is configured to be controlled by only fingers of the first hand while the second deflection actuator is configured to be controlled by only fingers of the second hand.

11. The medical device of claim 1, further including a split tube having a longitudinal opening extending along a substantial entirety of the split tube, wherein the split tube is configured to wrap around a shaft of an endoscope to secure the medical device to the endoscope.

12. A medical device, comprising:
    a shaft;
    a first tool extending from a distal end of the shaft;
    a second tool extending from the distal end of the shaft; and
    a control assembly coupled to the shaft, the control assembly having a longitudinal axis and including:
        a first set of controls disposed on a first grip on a first side of the longitudinal axis of the control assembly, the first set of controls configured to control one or more of the deflection of the first tool from a longitudinal axis of the first tool, the rotation of the first tool about the longitudinal axis of the first tool, or movement of the first tool along the longitudinal axis of the first tool; and
        a second set of controls disposed on a second grip on a second side of the longitudinal axis of the control assembly that is opposite of the first side, wherein the second set of controls is configured to control one or more of the deflection of the second tool from a longitudinal axis of the second tool, the rotation of the second tool about the longitudinal axis of the second tool, or movement of the second tool along the longitudinal axis of the second tool.

13. The medical device of claim 12, wherein the first set of controls and the second set of controls are mirror images of one another about the longitudinal axis of the control assembly.

14. The medical device of claim 12, wherein the first set of controls is configured to control two or more of the deflection of the first tool from a longitudinal axis of the first tool, the rotation of the first tool about the longitudinal axis of the first tool, or movement of the first tool along the longitudinal axis of the first tool.

15. The medical device of claim 14, wherein the second set of controls is configured to control two or more of the deflection of the second tool from a longitudinal axis of the second tool, the rotation of the second tool about the longitudinal axis of the second tool, or movement of the second tool along the longitudinal axis of the second tool.

16. A medical device, comprising:
    a shaft;
    a first tool and a second tool each extending from a distal end of the shaft; and a control assembly coupled to the shaft, the control assembly including:
a console,
a first grip extending proximally from the console;
a second grip extending proximally from the console:
a first deflection actuator configured to deflect the first tool about a first longitudinal axis of the first tool, and a second deflection actuator configured to deflect the second tool about a second longitudinal axis of the second tool;
a first rotation actuator configured to rotate the first tool about the first longitudinal axis of the first tool, and a second rotation actuator configured to rotate the second tool about the second longitudinal axis of the second tool; and
a first longitudinal actuator configured to move the first tool along the first longitudinal axis of the first tool; wherein the first rotation actuator, the first deflection actuator, and the first longitudinal actuator each extends from different offset surfaces of the control assembly, and a second longitudinal actuator configured to move the second tool along the second longitudinal axis of the second tool;

wherein the first grip is configured to be held by a first hand of an operator, and the second grip is configured to be held by a second hand of the operator, wherein the first deflection actuator, the first rotation actuator, and the first longitudinal actuator are configured to be controlled by only fingers of the first hand while the second deflection actuator, the second rotation actuator, and the second longitudinal actuator are configured to be controlled by only fingers of the second hand.

17. The medical device of claim 16, wherein the first grip is fixed relative to the console, and the second grip is fixed relative to the first grip.

18. The medical device of claim 16, wherein at least one of the first grip and the second grip is releasably coupled to the console.

19. The medical device of claim 16, further including a split tube having a longitudinal opening extending along a substantial entirety of the split tube, wherein the split tube is configured to wrap around a shaft of an endoscope to secure the medical device to the endoscope.

\* \* \* \* \*